United States Patent [19]

Brain

[11] Patent Number: 4,995,388
[45] Date of Patent: Feb. 26, 1991

[54] ARTIFICIAL AIRWAY DEVICE

[76] Inventor: Archibald I. Brain, 10 Preston Drive, Wanstead, London E11, England

[21] Appl. No.: 512,791

[22] Filed: Mar. 22, 1990

[30] Foreign Application Priority Data

Mar. 22, 1989 [GB] United Kingdom ............ 8906570

[51] Int. Cl.⁵ ............................................ A61M 16/00
[52] U.S. Cl. ................................. 128/207.15; 604/96; 604/100; 128/207.14
[58] Field of Search .................. 128/207.15, 206.26, 128/207.14, 207.16; 604/96–103

[56] References Cited

U.S. PATENT DOCUMENTS

| | | | |
|---|---|---|---|
| 4,235,239 | 11/1980 | Elam | 128/207.15 |
| 4,327,720 | 5/1982 | Bronson et al. | 604/97 |
| 4,509,514 | 4/1985 | Brain | 128/207.15 |

Primary Examiner—Edgar S. Burr
Assistant Examiner—Stephen R. Funk
Attorney, Agent, or Firm—Sughrue, Mion, Zinn, Macpeak and Seas

[57] ABSTRACT

An artificial airway device, for use in place of an endotracheal tube to facilitate lung ventilation in an unconscious patient, is in the form of a laryngeal mask comprising an airway tube opening into the interior space of lumen of a mask portion whose periphery, which may be inflatable, is adapted to seal around inlet to the larynx, thus securing the patient's airway and permitting spontaneous or controlled ventilation. Drainage from the anterior region of the mask or directly from the oesophagus is provided by suitably arranged drainage tubes arranged for insertion with the mask. A soft, flexible upstanding collar is carried by the periphery of the mask, so as to surround the lumen of the mask and improve the sealing contact with the tissues around the circumference of the laryngeal inlet.

13 Claims, 5 Drawing Sheets

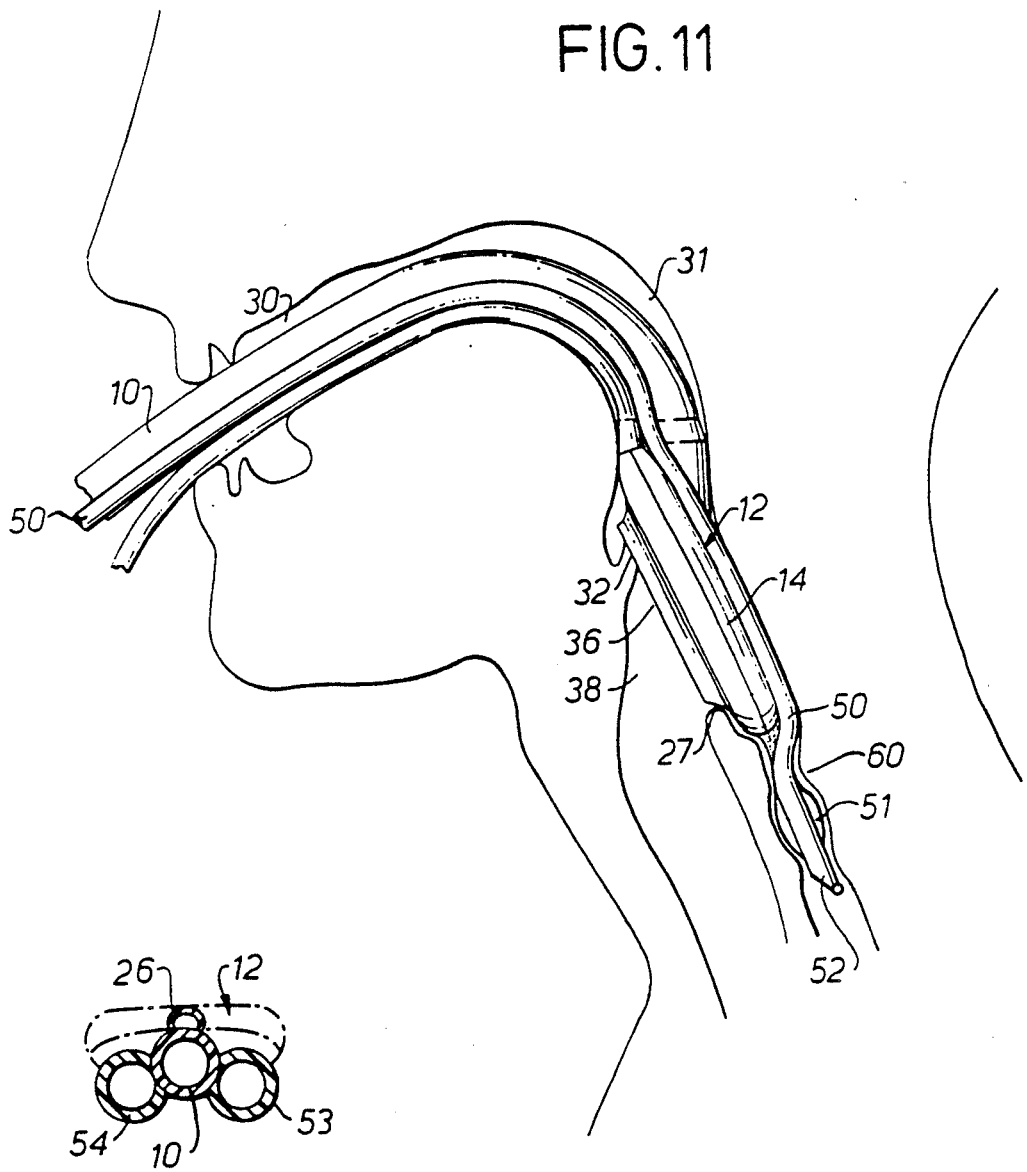

ARTIFICIAL AIRWAY DEVICE

FIELD OF THE INVENTION

This invention relates to artificial airway devices to facilitate lung ventilation in unconscious patients, and more specifically to such devices designed for placing in the oropharynx of the patient in order to prevent airway obstruction and to permit either spontaneous or controlled ventilation.

BACKGROUND TO THE INVENTION

To maintain the airway of an unconscious patient, and to achieve the objectives mentioned above, it is normal practice in general anaesthesia to use an endotracheal tube, which is a flexible tube of rubber or plastics, usually with an inflatable cuff around the distal end. Alternatively, an oro- or naso-pharyngeal airway may be used, which is a flexible tube extending from the mouth or nose into the pharynx but not into the larynx, and which is used in conjunction with a face mask, unlike the endotracheal tube. While preventing obstruction of the airway by the tongue, the oro- or nasopharyngeal airway cannot conveniently be used for controlled ventilation and does not prevent inhalation of extraneous matter.

The endotracheal tube is introduced through the larynx into the trachea or windpipe, whereupon the cuff is inflated through a small auxiliary tube to seal against the wall of the trachea. Introduction of the endotracheal tube is a skilled operation normally requiring use of a laryngoscope to guide the tube through the larynx, past the vocal cords and into the trachea. There is a risk that the tube or the laryngoscope may cause damage to soft tissues or to the sensitive structure of the larynx. It is not alway possible to see the larynx, making intubation difficult or impossible in some patients. There can be a risk of accidental intubation of the oesophagus or of the right or left main bronchus. Placing of the tube in the trachea effectively narrows the interior passage or lumen of the trachea and provides a potential source of damage through infection or pressure while preventing normal upward flow of mucus from the trachea and rendering effective coughing impossible.

In my British Pat. Specification No. 2111394B, I have described and claimed an artificial airway device comprising a curved or flexible tube and a mask portion carried at one end of the tube, the mask portion having a flexible annular peripheral formation which may be inflatable and which surrounds a hollow interior space or lumen of the mask portion, said annular peripheral formation of the mask portion being pre-formed with a roughly elliptical shape such as to be capable of conforming to, and of fitting readily within, the actual and potential space behind the larynx so as to form a seal around the circumference of the laryngeal inlet without the device penetrating into the interior of the larynx, the tube opening into the lumen of the mask portion to provide the airway with the axis of the tube substantially aligned with the length of the roughly elliptical annular peripheral formation of the mask portion. The device thus constitutes a laryngeal mask. In practice, the annular peripheral formation has been made as an inflatable tube, e.g. of a silicone rubber.

This device has proved successful in use. Insertion of the device has been found to be easy and convenient in the majority of patients. A laryngoscope is not usually required. The mask does not enter the larynx or trachea so the risk of damage to these structures is avoided and the tracheal lumen is not narrowed as it is by insertion of an endotracheal tube. The risk of accidental entry into the oesophagus or one of the main bronchi is also avoided. Once in place the laryngeal mask generally permits the lungs to be ventilated by positive pressure. Alternatively the patient may be permitted to breathe spontaneously.

To avoid the risk that the epiglottis could obstruct the airway by falling inwards into the lumen of the mask and blocking the opening of the tube therein, which could happen, for example, with small displacements of the mask which may occur during surgery or manipulation of the patient on the operating table, I have described in my Pat. Application No. 8713173 (Publication No. 2205499A) an artificial airway device of the kind described above wherein the airway tube opens into the lumen of the mask through an aperture which is provided with means, such as flexible cross-bars, to prevent it from being obstructed by the epiglottis while permitting passage of a second smaller tube, when required. Such a tube may be, for example, an endotracheal or endobronchial tube or a suction catheter, or an inspection tube such as a fibre-optic broncho- or laryngoscope.

The seal around the circumference of the laryngeal inlet which has been achieved, using an inflatable annular peripheral formation of the mask, has been found fully adequate in most circumstances. There are occasions, however, when an improved seal could be advantageous, e.g. to reduce the possibility that air might be allowed into the stomach when the patient's lungs are being ventilated under positive pressure, or to reduce the possibility that food regurgitated from the stomach might enter the lumen of the mask and the larynx. It is an object of one aspect of the invention to provide an improved seal around the circumference of the laryngeal inlet.

SUMMARY OF THE INVENTION

According to one aspect of the invention there is provided an artificial airway device to facilitate lung ventilation in an unconscious patient, comprising an airway tube and a mask carried at one end of the airway tube, the mask having a flexible annular peripheral formation of roughly elliptical shape capable of conforming to, and of readily fitting within, the actual and potential space behind the larynx so as to form a seal around the circumference of the laryngeal inlet without the device penetrating into the interior of the larynx, the annular peripheral formation surrounding a hollow interior space or lumen of the mask into which the airway tube opens, characterised in that the annular peripheral formation carries a soft, flexible, upstanding collar surrounding the lumen of the mask so as to improve the sealing contact with the tissues around the circumference of the laryngeal inlet.

Preferably the collar is formed of a flexible sheet material, and is adhered at its base to the adjacent surface of the annular peripheral formation.

In a preferred arrangement of the mask the inflatable peripheral formation is formed as a tubular ring and the collar is curved, as seen in cross-section, in the reverse sense to the walls of the tubular ring, so that the base of the collar is parallel to the adjacent surface of the ring and its free end extends away from the lumen of the mask.

The tube and collar may be made of a silicone rubber sheet material of similar thickness to one another.

Even with the improved seal achievable with the collar, there is a risk in some circumstances that if the contents of the stomach are regurgitated they will travel from the oesophagus and enter the bronchial tubes. The introduction of foreign matter into the lungs, known as aspiration, should be avoided.

According to another aspect of the present invention, there is provided an artificial airway device to facilitate lung ventilation in an unconscious patient, comprising an airway tube and a mask carried at one end of the airway tube, the mask having a flexible annular peripheral formation of roughly elliptical shape capable of conforming to, and of readily fitting within, the actual and potential space behind the larynx so as to form a seal around the circumference of the laryngeal inlet without the device penetrating into the interior of the larynx, the annular peripheral formation surrounding a hollow interior space or lumen of the mask into which the airway tube opens, wherein the artificial airway device further comprises a drainage tube having one end region arranged for insertion with the mask and the other end capable of being positioned below the patient for extracting fluid from the area of the mask by syphonic action, or of being connected to suction apparatus for extracting such fluid by suction.

In a first embodiment, the drainage tube is of smaller diameter than the airway tube so that it may be accommodated in the airway tube, said one end region opening into the lumen of the mask.

In a second embodiment, when the mask has an upstanding collar surrounding the lumen of the mask, the said one end region of the drainage tube may be forked and adhered to the outside of a part of the periphery of the collar, with openings of the fork portions being arranged to extract fluid from the area around the exterior of the mask.

The first and second embodiments are appropriate to drain any fluid which has already entered the larynx from the oesophagus. This may be sufficient when it is known that the stomach of the patient was empty before intubation. However, in cases where the patient may have gastric contents, particularly in emergency cases, it is appropriate to arrange for fluid drainage directly from the oesophagus. To this end, the third and fourth embodiments have in common a drainage tube the said one end region of which opens into the oesophagus when the mask has been inserted into the laryngeal space.

In the third embodiment, the said one end region of the drainage tube extends past the distal end of the mask so as to pass through the upper oesophageal sphincter muscle. The drainage tube bifurcates at the distal end of the mask to provide fork portions lying adjacent respective lateral posterior surfaces of the flexible annular peripheral formation.

An inflatable cuff can be provided around the region of the drainage tube which will lie in the oesophagus below the sphincter muscle to seal the tube and minimise the risk of fluid regurgitation around the sides of the tube.

In the fourth embodiment, the said one end region of the drainage tube extends as far as the distal end of the mask so that its opening lies against, but does not pass through, the upper oesophageal sphincter muscle.

BRIEF SUMMARY OF THE DRAWINGS

Specific embodiments of the invention will now be described in more detail by way of example and with reference to the accompanying drawings, in which:

FIG. 8 is a section along line VIII—VIII of FIG. 7;

FIG. 11 shows diagrammatically the third embodiment in use in a patient.

DETAILED DESCRIPTION OF THE PREFERRED EMBODIMENTS

Figure 1:
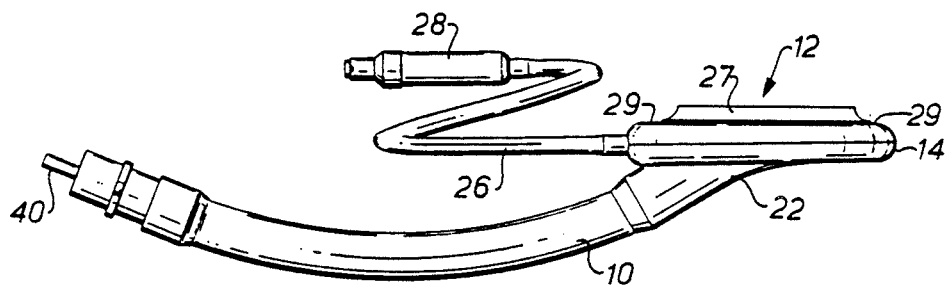
FIG. 1 is a side view of an artificial airway device in the form of a laryngeal mask.

The laryngeal mask illustrated in FIGS. 1 to 4 of the drawings comprises a flexible airway tube 10 of silicone rubber material, similar to that used for some endotracheal tubes, and a mask 12 of flexible silicone rubber sheet material, having an inflatable tubular ring 14 of the same silicone rubber material forming its periphery and a web 16 which closes off the rear of the interior or lumen 18 of the mask and is formed with an aperture 19. The distal end 20 of the airway tube 10 is secured, as by welding, in one end of a short piece 22 of thick-walled silicone rubber tubing whose other end is moulded to fit against the outer edge of the web 16 and around the aperture 19, so as to form a semi-rigid backpiece for the mask, which backpiece carries the airway tube 10 at an angle of substantially 30° to the plane of the ring 14. The airway tube 10 thus opens into the interior or lumen 18 of the mask 12 through the piece 22 and the aperture 19. The peripheral ring 14 is of roughly elliptical shape as seen in plan (FIG. 2) though its distal end 15 may be slightly elongated to conform with the triangular shape of the base of the hypopharynx where it becomes continuous with the upper end of the oesophagus. The airway tube 10 lies in substantially the same plane as the major axis of the peripheral ring 14 and at substantially 30° to the plane of the ring 14. The ring 14 is formed with a part 24 into which is sealed one end of a flexible silicone rubber tube 26 of much smaller diameter. The other end of tube 26 is provided with an inflation indicator 28, and can be connected to a small pump (not shown) such as a disposable 20 ml medical syringe for inflation of the ring 14. Alternatively the tube 26 may be permanently connected through a valve to a collapsible bulb whose capacity is equal to the optimal inflated capacity of the ring 14.

The aperture 19 through which the airway tube 10 opens into the lumen 18 of the mask 12 is provided with two flexible cross-bars 21 extending across the aperture 19 substantially parallel with the major axis of the peripheral ring 14, so as to leave the middle of the aperture clear for passage of an inspection or other tube. The bars 21 effectively prevent the epiglottis from falling into the aperture 19 and obstructing the airway.

A soft flexible upstanding collar 27, surrounding the lumen 18 of the mask, is formed of flexible sheet material, e.g. of a silicone rubber sheet material of similar thickness to that of the tubular ring 14. The collar 27 is adhered at its base to the adjacent surface 29 of the ring 14, and is curved, as seen in cross-section in FIG. 3, in the reverse sense to the walls of the ring 14, so that the base of the collar 27 is parallel to the adjacent surface 29 of the ring 14 and its free end extends away from the lumen 18 of the mask. The collar 27 is designed to offer a low profile on deflation of the ring 14, to assist insertion and removal of the laryngeal mask. When the laryngeal mask is in place and the ring 24 is inflated, the collar 27 is found to improve the effectiveness of the seal between the mask and the tissues of the laryngeal inlet by about 30% on average, and thereby to reduce the risk of allowing air under positive pressure into the stomach and to improve the exclusion of any regurgitated food from the interior of the mask and hence from the larynx.

Figure 2:
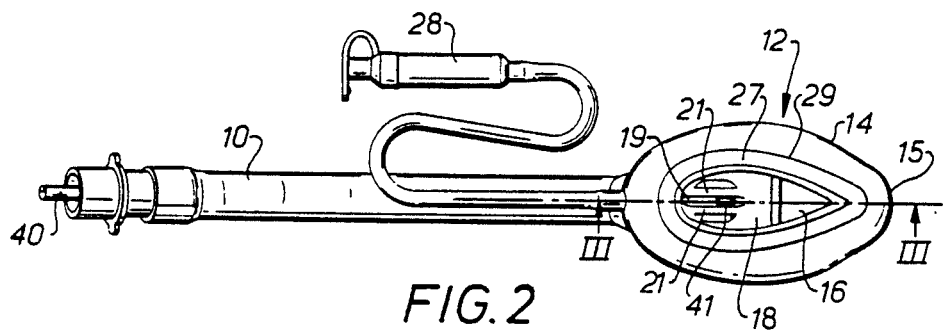
FIG. 2 is a plan view of the device with the periphery of the mask portion inflated.
Figure 3:
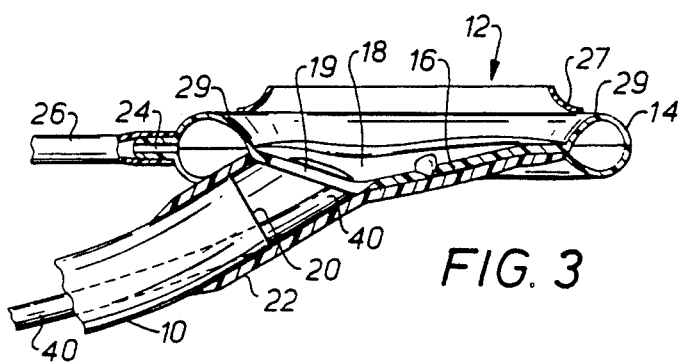
FIG. 3 is a section on the line III—III of FIG. 2.
Figure 4:
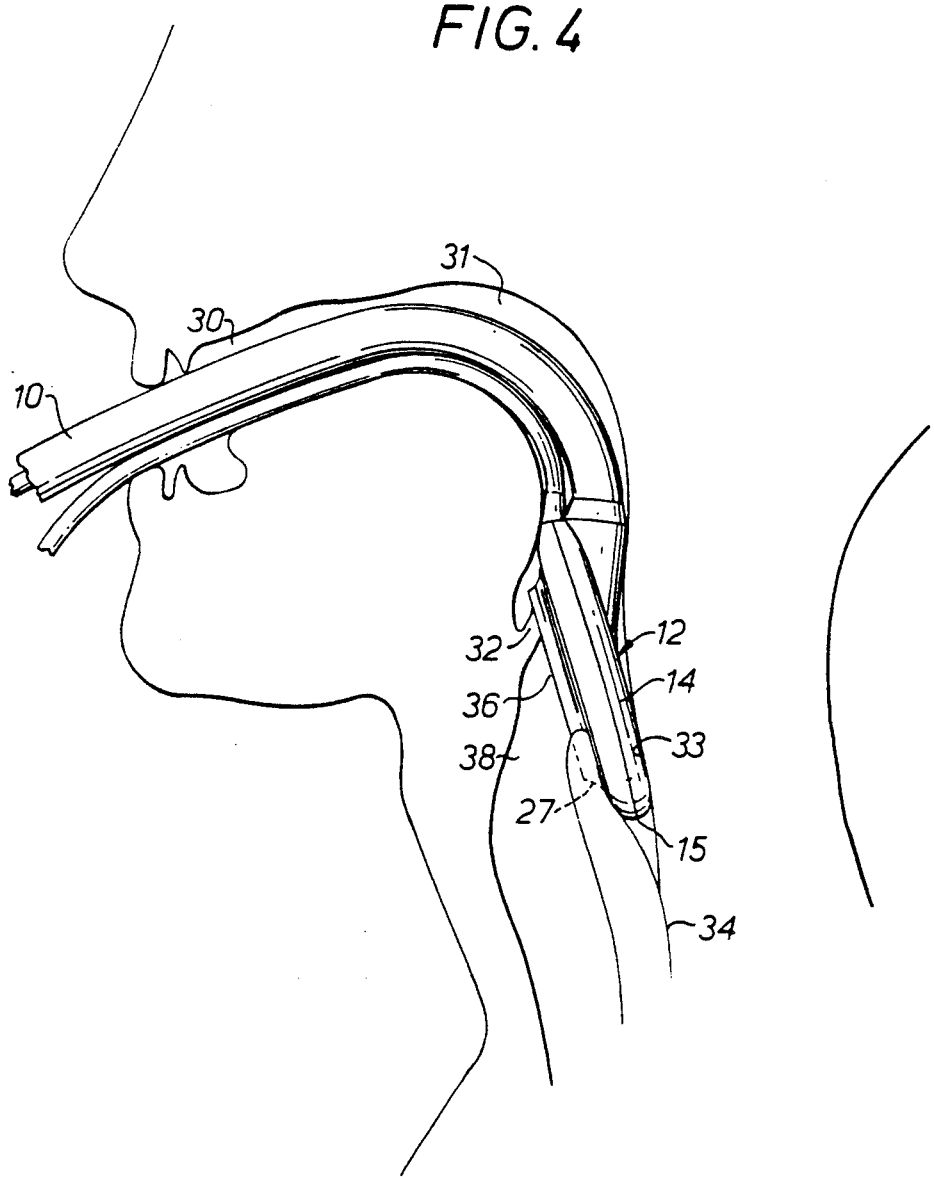
FIG. 4 shows diagrammatically the device in position for use in a patient.

In some circumstances it can be advantageous to provide a small diameter drainage tube, as shown at 40 in FIGS. 1 to 3, accommodated in the airway tube 10, with one end 41 opening into the lumen 18 of the mask and the other end of sufficient length to be capable of being positioned below the patient for extracting fluid from the lumen of the mask by syphonic action, or of being connected to suction apparatus for extracting fluid by suction.

Different sizes of mask are needed for different sizes of patient. In use, the ring 14 is first fully deflated and the device is inserted through the patient's mouth 30 and down through the throat 31 past the epiglottis 32 until the mask 12 comes to rest in the position shown in FIG. 4, with the distal end 15 of the ring 14 in the base 33 of the throat, lying against the upper end of the normally closed oesophagus 34, which the mask cannot easily enter provided that the correct size has been chosen. The ring 14 is then inflated as shown to increase the sealing pressure around the inlet 36 to the larynx 38. The collar 27 is flattened between the ring 14 and the inlet 36 to improve the seal. The patient's airway is thus secure and unobstructed and the laryngeal mask can be connected directly to conventional anaesthetic circuit hosing for either positive pressure or spontaneous breathing. As can be seen from FIG. 4, the airway tube 10 opens into the lumen of the mask 12 at the appropriate angle (substantially 30°) to enable an inspection or other tube (not shown) passed through the airway tube 10 and the mask 12 to emerge at the correct angle for intubation of the larynx 38.

Figure 5:
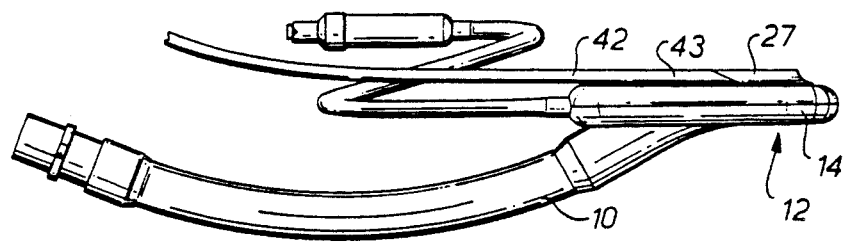
FIG. 5 is a side view of a second embodiment of the laryngeal mask.
Figure 6:
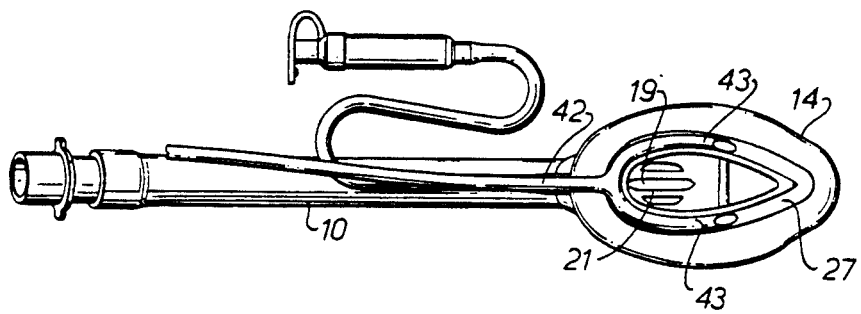
FIG. 6 is a plan view of the device of FIG. 5.

As shown in FIGS. 5 and 6, a small diameter drainage tube 42 may be provided, with a forked end 43 adhered to the outside of the collar 27 around a part of its periphery, so as to be capable of extracting fluid or regurgitated fluids from the area around the exterior of the mask. Again the end of the drainage tube 42 should be capable of being positioned below the patient to allow extraction of fluid by syphonic action, or of being connected to suction apparatus for extraction of fluid by suction.

The drainage tubes 40 and 42 opening into the anterior region of the mask are suitable for removing foreign matter which has travelled from the oesophagus into the interior of the mask, to prevent such matter from entering the larynx. In some circumstances however, particularly where it is suspected that the stomach of the patient may have contents, a different form of drainage tube can be provided.

Figure 7:
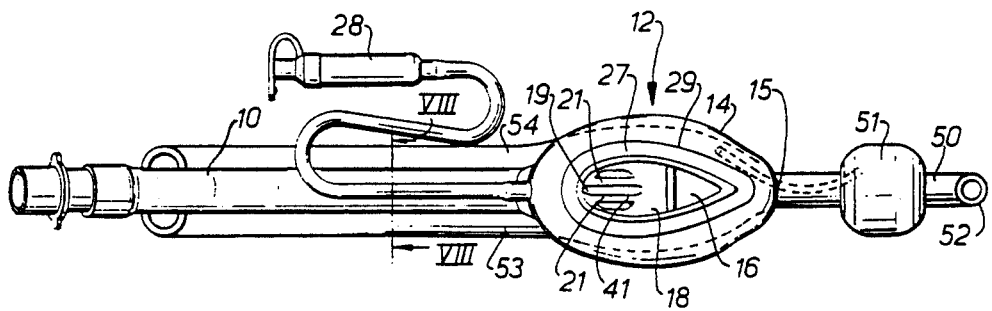
FIG. 7 is a plan view of a third embodiment of the laryngeal mask.

In FIG. 7, a drainage tube 50 is provided having an end region of a length such that it extends past the distal end 15 of the mask 12 and passes through the upper oesophageal sphincter muscle. An inflatable cuff 51 is provided around the region of the tube which will lie below the sphincter muscle to provide a seal. The end region of the tube 50 has an anterior facing bevel 52 so as to prevent the tube pushing down the epiglottis or accidentally entering the larynx. The tube 50 bifurcates at the distal end 15 of the mask 12 into two fork portions 53,54 which are secured respectively to the posterior lateral surfaces of the peripheral formation 14. This is shown in FIG. 8. Use of the embodiment of FIG. 7 is shown in FIG. 11. As the mask 12 is inserted, the tube 50 passes through the oesophageal sphincter muscle 60 and enters the oesophagus. The inflatable cuff 51 is then inflated, and this can be done using the same air tube 26 which inflates the peripheral formation 14 of the mask 12. Regurgitated food or fluid from the stomach thereby enters the tube 50 and is removed by syphonic action or suction without entering the larynx.

Figure 9:
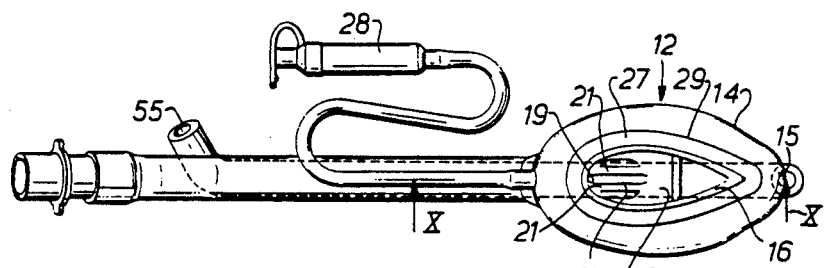
FIG. 9 is a plan view of a fourth embodiment of the laryngeal mask.
Figure 10:
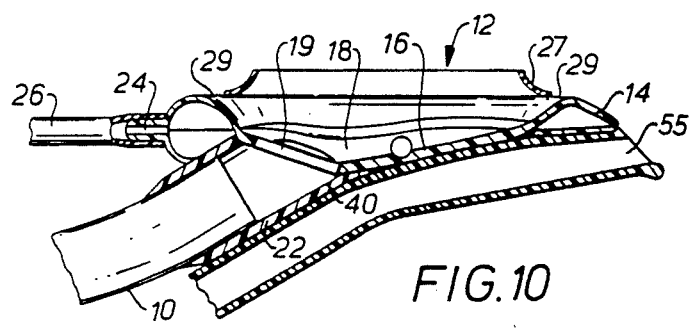
FIG. 10 is a section along line X—X of FIG. 9.

The embodiment of FIGS. 9 and 10 differs from that shown in FIGS. 7 and 8 in that there is a single continuous drainage tube 55 which is secured to the posterior surface of the mask 12 and the length of which extending as far as the distal end of the mask 12 is shorter than the corresponding length of the tube 50 in the embodiment of FIG. 7 and 8. The tube 55 is arranged to lie facing the oesophageal sphincter muscle but not to extend through it. This is less invasive than the embodiment of FIG. 7 and 8. The drainage tube 55 similarly serves to remove regurgitated food or fluid from the oesophagus. The tube 55 has a bevelled edge 64 which is beaded to avoid damage to tissues during insertion.

The embodiments described above may be used as a disposable instrument or as a re-usable one.

Although only a single collar 27 has been described above and shown in the accompanying drawings, it would be possible for the ring 14 to carry two or more such collars, disposed parallel to and one within the other.

The tube and mask portion could be made of other sterilisable materials, such as plastics. The materials may be more rigid than the inflatable silicone rubber materials described above. With some materials it may not be necessary that the peripheral ring should be inflatable. For example, the ring 14 may consist of a foam material within an air-tight covering, from which the air is evacuated to facilitate insertion of the mask. In any case the mask 12 will be shaped as described above to conform to and fit readily into the actual and potential space behind the larynx and to seal around the laryngeal inlet. The reference to actual and potential space will be understood to refer to the space normally available and that which can become available on flexure of the surrounding structures.

The drainage tubes may be fixedly secured to the mask and inserted with it. Alternatively, the drainage tubes need not be fixed to the mask but can be movable longitudinally of it, so that the drainage tubes could be introduced after the laryngeal mask has been placed in position.

It is possible to utilise the bifurcated tube illustrated in FIG. 7 but to replace the intraoesophageal drainage portion 50 with a shorter drainage portion terminating at the distal end region 15 of the mask as shown in FIG. 9.

What is claimed is:

1. An artificial airway device to facilitate lung ventilation in an unconscious patient, comprising an airway tube and a mask carried at one end of the airway tube, the mask having a flexible annular peripheral formation of roughly elliptical shape capable of conforming to and of readily fitting within the actual and potential space behind the larynx so as to form a seal around the circumference of the laryngeal inlet without the device penetrating into the interior of the larynx, the annular peripheral formation surrounding a hollow interior space or lumen of the mask into which the airway tube opens, and carrying a soft flexible upstanding collar surrounding the lumen of the mask, wherein the artificial airway device further comprises a drainage tube having one end region arranged for insertion with the mask and the other end capable of being positioned below the patient for extracting fluid from the area of the mask by syphonic action, or of being connected to suction apparatus for extracting such fluid by suction.

2. An artificial airway device according to claim 1 wherein the drainage tube is of a smaller diameter than the airway tube so that it may be accommodated in the airway tube and wherein said one end region opens into the lumen of the mask.

3. An artificial airway device according to claim 1 wherein the said one end region of the drainage tube is forked and is adhered to the outside of a part of the periphery of the upstanding collar, with openings of the fork portions being arranged to extract fluid from the area around the exterior of the mask.

4. An artificial airway device according to claim 1 wherein the said one end region of the drainage tube extends past the distal end of the mask so as to pass through the upper oesophageal sphincter muscle when the mask is in use in a patient, the drainage tube being bifurcated at the distal end of the mask to provide fork portions lying adjacent respective lateral posterior surfaces of the flexible annular peripheral formation.

5. An artificial airway device according to claim 4 wherein an inflatable cuff is provided around the region of the drainage tube which will lie in the oesophagus below the sphincter muscle when the mask is in use in a patient.

6. An artificial airway device as claimed in claim 1 wherein the said one end region of the drainage tube extends as far as the distal end of the mask so that its opening lies against, but does not pass through, the upper oesophageal sphincter muscle when the mask is in use in a patient.

7. An artificial airway device to facilitate lung ventilation in an unconscious patient, comprising an airway tube and a mask carried at one end of the airway tube, the mask having a flexible annular peripheral formation of roughly elliptical shape capable of conforming to, and of readily fitting within, the actual and potential space behind the larynx so as to form a seal around the circumference of the laryngeal inlet without the device penetrating into the interior of the larynx, the annular peripheral formation surrounding a hollow interior space or lumen of the mask into which the airway tube opens, characterised in that the annular peripheral formation carries a soft, flexible, upstanding collar surrounding the lumen of the mask so as to improve the sealing contact with the tissues around the circumference of the laryngeal inlet.

8. An artificial airway device according to claim 7 wherein the collar is formed of a flexible sheet material, and is adhered at its base to the adjacent surface of the annular peripheral formation.

9. An artificial airway device according to claim 1 or 7 wherein the flexible annular peripheral formation is inflatable.

10. An artificial airway device according to claim 9 wherein the inflatable peripheral formation is formed as a tubular ring and the collar is curved, as seen in cross-section, in the reverse sense to the walls of the tubular ring, so that the base of the collar is parallel to the adjacent surface of the ring and its free end extends away from the lumen of the mask.

11. An artificial airway device according to claim 10 wherein the tubular ring and collar are made of a silicone rubber sheet material of similar thickness to one another.

12. An artificial airway device to facilitate lung ventilation in an unconscious patient, comprising an airway tube and a mask carried at one end of the airway tube, the mask having a flexible annular peripheral formation of roughly elliptical shape capable of conforming to and of readily fitting within the actual and potential space behind the larynx so as to from a seal around the circumference of the laryngeal inlet without the device penetrating into the interior of the larynx, the annular peripheral formation surrounding a hollow interior space or lumen of the mask into which the airway tube opens, wherein the artificial airway device further comprises a drainage tube having one end region arranged for insertion with the mask and the other end capable of being positioned below the patient for extracting fluid from the area of the mask by syphonic action, or of being connected to suction apparatus for extracting such fluid by suction, the said one end region of the drainage tube extending past the distal end of the mask so as to pass through the upper oesophageal sphincter muscle when the mask is in use in a patient, the drainage tube being bifurcated at the distal end of the mask to provide fork portions lying adjacent respective lateral posterior surfaces of the flexible annular peripheral formation.

13. An artificial airway device to facilitate lung ventilation in an unconscious patient, comprising an airway tube and a mask carried at one end of the airway tube, the mask having a flexible annular peripheral formation of roughly elliptical shape capable of conforming to and of readily fitting within the actual and potential space behind the larynx so as to form a seal around the circumference of the laryngeal inlet without the device penetrating into the interior of the larynx, the annular peripheral formation surrounding a hollow interior space or lumen of the mask into which the airway tube opens, wherein the artificial airway device further comprises a drainage tube having one end region arranged for insertion with the mask and the other end capable of being positioned below the patient for extracting fluid from the area of the mask by syphonic action, or of being connected to suction apparatus for extracting such fluid by suction, the said one end region of the drainage tube extending as far as the distal end of the mask so that its opening lies against, but does not pass through, the upper oesophageal sphincter muscle when the mask is in use in a patient.

* * * * *